(12) United States Patent
Kuchuk et al.

(10) Patent No.: US 7,244,876 B1
(45) Date of Patent: Jul. 17, 2007

(54) PROCESS OF RAPID VARIETY-INDEPENDENT PLANT TRANSFORMATION

(75) Inventors: Nikolay V. Kuchuk, Kiev (UA); Victor Klimyuk, Norwich (GB)

(73) Assignee: Icon Genetics, Inc., Princeton, NJ (US)

( * ) Notice: Subject to any disclaimer, the term of this patent is extended or adjusted under 35 U.S.C. 154(b) by 0 days.

(21) Appl. No.: 09/980,542

(22) PCT Filed: May 17, 2000

(86) PCT No.: PCT/US00/13555

§ 371 (c)(1),
(2), (4) Date: Mar. 4, 2002

(87) PCT Pub. No.: WO00/70019

PCT Pub. Date: Nov. 23, 2000

Related U.S. Application Data

(60) Provisional application No. 60/134,459, filed on May 17, 1999.

(51) Int. Cl.
*C12N 15/82* (2006.01)
*C12N 15/87* (2006.01)
*A01H 1/00* (2006.01)
*A01H 1/04* (2006.01)
*C12N 15/29* (2006.01)

(52) U.S. Cl. .................. 800/291; 800/260; 800/306; 800/312; 800/314; 800/317.2; 800/317.3; 800/320; 800/320.1; 800/320.2; 800/320.3; 435/462

(58) Field of Classification Search .............. 800/278, 800/320.3, 260, 269, 268, 320.1; 435/320.1; 536/23.1
See application file for complete search history.

(56) References Cited

U.S. PATENT DOCUMENTS

| | | | |
|---|---|---|---|
| 4,732,856 A * | 3/1988 | Federoff .................. | 800/291 |
| 5,482,852 A | 1/1996 | Yoder et al. | |
| 5,501,967 A | 3/1996 | Offringa et al. | |
| 5,750,828 A | 5/1998 | Eubanks | |
| 5,965,791 A | 10/1999 | Ebinuma et al. | |

FOREIGN PATENT DOCUMENTS

WO    WO-01/85969 A    11/2001

OTHER PUBLICATIONS

Zhang, et. al., Wheat embryogenesis and haploid production in wheat x maize hybrids, Euphytica 90: 315-324, 1996, p. 315.*
Jauhar, et. al. Chromosome-mediated and direct gene transfers in wheat, Genome 42: 570-583, 1999, pp. 572-573.*
(Hadley et. al., in Hybridization in Crop Plants, ed. Fehr & Hadley, Society of Agronomy and Crop Science Society of America, Madison, Wisconsin, p. 133).*
(Rieger et al., Glossary of Genetics & Cytogenetics, 1976, Springer-Verlag, NY, p. 511).*
Gleave et al. Plant Molecular Biology 40(2): 223-235 (May 1999).*
Dale et al. Proc. Natl. Acad. Sci. USA 88(23): 10558-10562 (Dec. 1991).*
Zhang et al. Theoretical and Applied Genetics 107(7): 1157-1168 (Nov. 2003).*
Gernand et al. The Plant Cell 17: 2431-2438 (Sep. 2005).*
Dudits, et al., "Transfer Of Resistance Traits From Carrot Into Tobacco By Asymmetric Somatic Hybridization: Regeneration Of Fertile Plants", Proc. Batl. Acad. Sci. USA. Dec. 1987, vol. 84, pp. 8434-8438, see pp. 8434-8437.
Puite, K,J, et al.: "Nuclear genomic composition of asymmetric fusion products between irradiated transgenic *Solanum brevidens* and *Solanum tuberosum*: Limited elimination of donor chromosomes and polyploidization of the recipient genome" Theoretical and Applied Genetics, vol. 86, No. 2-3, 1993, pp. 237-244.
Ow and Medberry, Critical Reviews in Plant Sciences, vol. 14, No. 3, pp. 239-261.
Carroll et al: Genetics: 139: 407-420(1995).

* cited by examiner

*Primary Examiner*—David T. Fox
(74) *Attorney, Agent, or Firm*—Lerner, David, Littenberg, Krumholz & Mentlik, LLP

(57) ABSTRACT

Disclosed is a method of making transgenic plants. Heterologous DNA is first introduced into a donor plant, plant cell or protoplast, and then moved from the donor to a recipient plant, plant cell or protoplast unaccompanied by any native genomic DNA of the donor. The donor and recipient are chosen that produce unstable progeny or demonstrate preferential segregation or sorting out. The DNA may be inserted randomly or at specific locations in the genome of the recipient plant. Also disclosed are transgenic plants produced by the methods, and plant progeny, plant parts and seeds and seed parts from the plants.

23 Claims, 6 Drawing Sheets

PROCESS OF RAPID VARIETY-INDEPENDENT PLANT TRANSFORMATION

CROSS REFERENCE TO RELATED APPLICATIONS

The present application is a 371 of International Application PCT/US00/13555, filed 17 May 2000, which claims benefit of the filing date of U.S. Provisional Patent Application Ser. No. 60/134,459, filed 17 May 1999. The disclosures of all of said applications are incorporated by reference herein.

FIELD OF THE INVENTION

The present invention relates to methods of introducing genetic material of interest into plants, and more particularly to methods involving transformation and line conversion of plant species that have proven difficult to manipulate on a genetic level.

BACKGROUND OF THE INVENTION

Methodologies have evolved during the last twenty years to genetically engineer plants. In general, they are based on either direct DNA introduction into plant cells or indirect transfer mediated by *Agrobacterium tumefaciens*. Methods involving direct transfer include particle bombardment of cultured plant tissues and DNA introduction into naked plant cells i.e., protoplasts, using polyethylene glycol or electroporation. See, e.g., Sawahel & Cove, *Biotech, Adv.* 10:394–412 (1992); Christou, *Cur. Opinion Biotech.* 4:135–141 (1993); Gelvin, *Cur. Opinion Biotech.* 9:227–232 (1998) and Birch, *Annu. Rev. Plant Physiol. Plant Mol. Biol,* 48:297–326 (1997). Most methods are variety-specific because they are based on use of in vitro grown regenerable plant systems which in turn are variety-specific. Except for a few economically important crops such as potato, tomato and canola, transformation methods available currently work with only a handful of varieties.

The traditional backcross method of breeding has provided a mechanism for the transfer of a trait from one line (the donor) to another line (the recurrent parent). See, e.g., Harlan and Pope, *J. Heredity,* 13:319–322 (1922). It has been particularly useful for corn, soybean and cotton. Successful backcross breeding requires: a previously derived recurrent parent; maintenance of the trait of interest during selection; and sufficient backcrosses to reconstitute the genome of the recurrent parent. Allard, *Principles of Plant Breeding,* Wiley and Sons (1960). During the backcross program, the hybrid population becomes increasingly homozygous for genes of the recurrent parent at a rate described by the formula:

Proportion of homozygosity=$1-0.5^m$ where m is the number of backcross generations. Using this formula, one can calculate that more than 98% of the hybrid genome will be homozygous for genes of the recurrent parent after six generations. The formula, however, only describes regions of the genome that are unlinked with respect to the genes being introgressed. The rate at which linked regions approach homozygosity is dependent upon the chromosome recombination frequency. In one of the most detailed studies assessing the effectiveness of traditional backcross breeding, eight Tm-2-converted isogenic lines of tomato were examined at nine flanking restriction fragment length polymorphism (RFLP) loci. See, Young and Tanksley, *Theor. Appl. Genet.* 77:353–359 (1989). The minimum donor chromosome fragment found after 10 generations of backcrossing and maintained without reduction in size for an additional nine generations was 4 cM the maximum size found even after 11 generations was 51 cM (i.e., more than half of the corresponding chromosome). In marker-assisted selection based on simple sequence repeats (SSR) or RFLP, the reconstruction could be done faster and cleaner, but it would require screening of sizable populations of progeny using relatively expensive methods and would be complicated by the random insertion of transgenes in independent primary transformants.

Plainly, backcrossing is not a trivial task because for most crop plants, hundreds of lines, hybrids or varieties are needed simultaneously. In 1998 for example, the U.S. soybean seed market consisted of over 500 varieties, and the U.S. maize seed market included over 600 hybrids. Another major disadvantage of the backcrossing method is that it is very time-consuming. Line conversion through recurrent backcrossing normally requires 3 to 5 subsequent backcrosses, thus adding at least two and sometimes up to four years to variety development time.

There are many disadvantages associated with current transformation methods. Line conversion, for example, is a process whereby heterologous DNA is transferred from one plant species or variety to another using various forms of sexual (i.e., pollination) or somatic (i.e., cellular) hybridization. Because current methods are species- and variety-specific, they can be commercially used only in combination with line conversion technologies that allow for transgene transfer from a primary transformant into multiple varieties of interest. In addition, they result in random transgene insertion into the host genome. Therefore, extensive screening of numerous independent transformation events are required in order to identify the events that are stable, inheritable and allow for proper transgene expression. Subsequent transgene insertions cannot be addressed to the same site, thus complicating breeding. Linkage drag (i.e., co-inheritance of unwanted traits) and a limited ability to handle multiple independent transgene traits present even further difficulties.

SUMMARY OF THE INVENTION

Applicants have invented a method of introducing nucleic acid into plants and producing genetically engineered plants. The methods are applicable to plants such as corn and wheat which have been quite difficult to genetically modify by existing technologies. In addition, the method constitutes a significant improvement over backcrossing methods because it achieves the same or better results in a much shorter time period.

The nucleic acid of interest is not introduced directly into the plant of interest or what is referred to as the recipient. Rather, it is first routed to another plant, different from the recipient, and which is referred to as the donor or the chipboard species. The nucleic acid is then moved from the donor to the recipient. One method entails sexual hybridization or "crossing" the two plants. Pollen from the donor is used to pollinate a recipient plant. Another method is conducted on the cellular level whereby cells or protoplasts of the donor and the recipient plants are fused. One feature of the invention allows for the nucleic acid to be moved from the donor to the recipient without the movement of any native genomic DNA of the donor. This is accomplished due to the selection of donor/recipient pairs that normally produce unstable hybrids. This means that the respective genomes are unstable and thus do not commingle so as to produce a "hybrid" plant. This phenomenon is hereinafter referred to as "producing unstable progeny or demonstrating preferential segregation or sorting out." During the temporary coexistence of the chromosomes of the donor and the recipient, the nucleic acid or the gene of interest is moved to the genome of the recipient plant. Another feature of the present invention accomplishes random or site-specific introduction of nucleic acid by surrounding the nucleic acid of interest with flanking sequences that allow transposition of the nucleic acid into a random location or direct the insertion of the nucleic acid into a specific location in the genome of the recipient.

Accordingly, one aspect of the present invention is directed to a method for introducing genetic material into plants, comprising:

preparing a first plant transformed with a heterologous nucleic acid having 5' and 3' excisable flanking sequences that allow movement of the heterologous nucleic acid from one genome to another;

crossing a second plant and the transformed first plant, wherein the first and second plants, upon crossing, produce unstable progeny or demonstrate preferential segregation or sorting out; and selecting progeny of the second plant of (b) which contain the heterologous nucleic acid.

In preferred embodiments, the 5' and 3' excisable flanking sequences comprise a transposable element, and the first plant, the second plant or both the first plant and the second plant produce a transposase specific to the transposable element. In another preferred embodiment, the 5' and 3' excisable flanking sequences are recombination sites and the first plant, the second plant or both the first and second plants produce a recombinase specific to the recombination sites.

In other preferred embodiments, the first plant, also refeeed to as to the donor or the clipboard species, is *Tripsacum* and in the second plant, also referred to as the recipient, is maize, wheat, barley or oat. In another preferred embodiment, the donor is *Orychophragmus* and the recipient is a crucifer such as canola. Other preferred donor/recipient pairs are: *Glycine tomentella*/soybean, *Solanum phreja*/potato, maize/wheat, maize/barley, maize/oat, *Pennisetum*/wheat, *Pennisetum*/barley, *Hordeum bulbosum*/barley, *Hordeum bulbosum*/wheat, *Nicotiana digluta*/*Nicotiana tabacum* and *Oryza minuta*/rice.

In other preferred embodiments, the donor and/or the recipient plant carries a Se semigamy mutation. In yet other preferred embodiments, the donor and/or recipient plant is soybean carrying a ms mutation causing polyembryony.

In other preferred embodiments of the process, transgenes are targeted into specific predefined genome sites through targeted recombination as an integrative locus.

A related aspect of the present invention is directed to a method for introducing genetic material into plants that is conducted on a somatic level. This method involves the following steps:

preparing a cell or protoplast of a first plant transformed with a heterologous nucleic acid having 5' and 3' excisable flanking sequences that allow movement of the heterologous nucleic acid from one genome to another;

fusing the cell or protoplast with a cell or protoplast of a second plant to produce a fused cell or a fused protoplast, wherein the first and second plants, upon crossing, produce unstable progeny or demonstrate preferential segregation or sorting out;

regenerating whole plants from the fused cell or the fused protoplast; and selecting progeny of the regenerated plants that contain the heterologous nucleic acid. The fused cells or protoplasts per se, are also provided. Further, the methods of the present invention produce plants that have a different genetic make-up than transgenic plants made by other methods because the end result of the process is an individual plant that is genetically devoid of any resident DNA of primary transformant (i.e., the donor). Progeny of the plant, plant parts and seed and seed parts from the plant are also provided.

The methods of the present invention provide for transgene manipulation in essentially all crop species, especially the economically important varieties. The methods are not only generally applicable to essentially all crop species, but they are rapid (one to two crosses), free of linkage drag and variety-independent. In addition, the methods described are the only variety-independent process of transformation and line conversion that can be used for genetic engineering of complex lines/hybrids which cannot be recovered after crosses with other varieties.

DETAILED DESCRIPTION OF THE INVENTION

Figure 1:
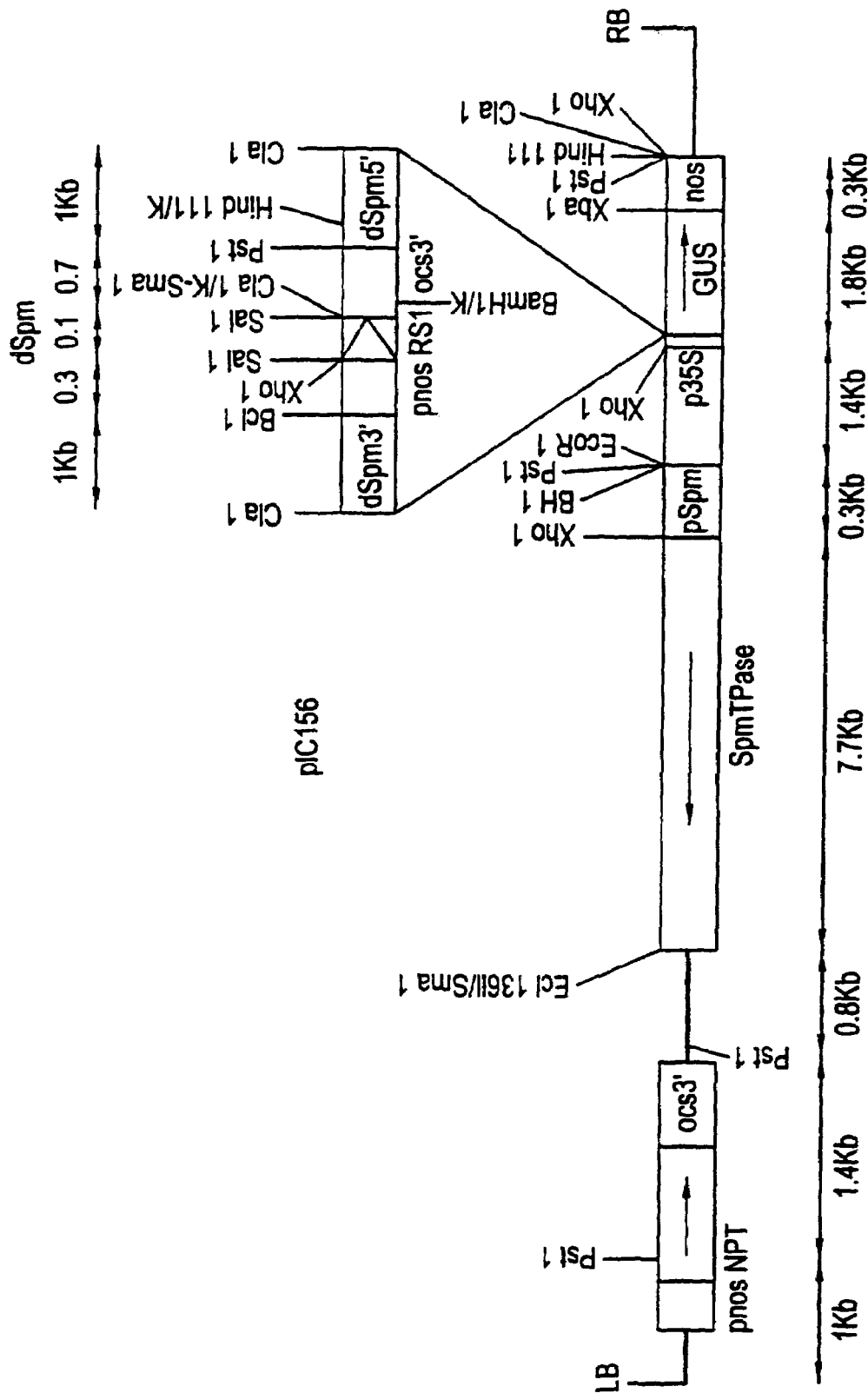
FIG. 1 is a linear plasmid map of pIC156.

The methods of the present invention produce transformed plants by transforming a donor species or mutant with a construct capable of excision/reinsertion, preferably by a transposon-mediated or homologous or non-homologous recombination mechanism, crossing the donor with a recipient, whereas donor and recipient organisms have been selected from species/mutant combinations that upon sexual/somatic hybridization produce hybrids that are unstable and demonstrate genome instability and segregation of one or both pure parental genotypes, inducing or selecting for excision of the heterologous nucleic acid from the recipient and integration into the donor parental chromosome, and lastly, selecting a progeny that is essentially a genetically pure recipient plant that carries the transgene in question. The flow of heterologous genetic material is completely separated from resident gene flow during genetic manipulations by utilizing species or mutant combinations of recipient and donor organisms that upon sexual/somatic hybridization produce hybrids that show no recombination between homologous/homologous chromosomes and which are unstable and upon mitotic or meiotic divisions, sort out pure parental genomes of one or both types.

By the term "plant", it is meant to include all flowering plants, and all forms, lines and varieties of the plant. "Transformed" is used herein to mean genetically modified by the incorporation of heterologous DNA into cells. By the term "heterologous", it is meant DNA not normally found in the recipient plant.

Species-specific chromosome elimination (genome segregation) in interspecific/intergeneric hybrids is a well-documented phenomenon. In many cases, however, unstable hybrids were of limited interest as the main breeding efforts were aimed at chromosome exchange between two parental genomes as a method for introgression of alien chromosomal material. Prior to the time the present invention was made, unstable hybrids segregating parental genomes were described only in terms of systems that produce haploid plants (interspecific, intergeneric crosses for production of haploid wheat, barley, or potato) or in terms of negative results of attempts to achieve an introgression of chromosome material from wild species into cultivated crops (such as from *Tripsacum* to maize or *Glycine tomentella* to soybean).

In general, for every crop species (including all varieties and lines thereof), there is a wild relative or a mutant form, that, upon hybridization, forms an unstable hybrid and can serve as a donor or clipboard plant as defined herein. An empirical way to identify such an organism involves crossing a crop species of interest with a number of related species and testing the genetic makeup of the resulting progeny. Methods of preliminary identification of progeny that is predominantly uniparental are known in the literature and are based on different selective or non-selective traits. Methods of broad and reliable genotyping of the progeny are numerous, simple, and rely on analysis of various markers in genomic DNA. Based on such primary screening and subsequent genotyping, suitable clipboard organisms can be rapidly identified. Beyond this basic criterion, the donor/recipient pairs are chosen so as to provide a an adequate duration of the hybrid state in cells of primary hybrid, or of its progeny. While complete elimination is a desired end state, relative duration of coexistence of chromosomes of both species in the same cell is important as it provides sufficient time for the excision of transgene locus from the "clipboard" organism and its integration into the chromosome of recipient's chromosome.

Physical interaction and in particular, chromosome material exchange between parental genomes in a hybrid, can be excluded or minimized in a number of different ways. The most well-known approach is based on the use of interspecific or integeneric hybridization—the hybrids produced show little if any homologous chromosome pairing, thus limiting crossover. In addition, many of such hybrids are more or less genetically unstable and show tendency for a rapid elimination of one parental genome. As a result, by using such a cross, the chromosomes of two remote parental organisms may be placed in a hybrid nucleus to produce a hybrid state for directed exchange of transgene material between the parents. However, resident chromosome material of the two parents essentially does not interact, and subsequent chromosome elimination will allow for elimination of one parent as soon as $F_0$, $F_1$ or $BC_1$ progeny.

In addition to hybridization between remote species as a process that allows for a temporary hybrid state followed by rapid recovery of pure parental genomes, there are other approaches that achieve similar results. One such approach is based on the use of mutants that reduce or eliminate chromosome crossover and/or those that cause pure parental genome segregation in intra-specific as well as interspecific crosses. One example is semigamy in cotton, a mutation which causes sperm nucleus to enter egg cell but subsequent nuclear fusion supposedly does not take place and both nuclei divide independently resulting in $F_1$ plants that are chimeral for sectors of haploid tissues of paternal and maternal type. See, Turcotte and Feaster, *J. Hered.* 58:55–57 (1967). Another approach is the well-characterized *Oenothera* system in which all chromosomes are involved in translocations in such a way that the $F_1$ crosses with normal stocks will have at meiosis a ring containing the entire haploid number of chromosomes, thus excluding independent chromosome sorting out. A further approach to the use of chemical/physical treatments such as irradiation (Pandey, *N. Z. J. Bot.*, 18:203–207 (1980)) or other, of one parent that result in a damage and subsequent preferential elimination of damaged genome. Such an approach has been instrumental in production of gynogenetic onion plants after pollinating with gamma-irradiated pollen. See, Dore & Marie, *Plant Breeding* 111:142–147 (1993).

To carry out the present invention for any given plant, wild or remote relative can be found that allows for genetically unstable hybrids that are characterized by rapid genome segregation. Well-characterized combinations involving economically important crops are summarized below.

Insofar as dicotyledonous crops are concerned, the best studied case for potato is a hybridization between commercial varieties of potato, *Solanum tuberosum,* and a wild species *Solanum phureja,* that results in high frequency of haploid production as a result of early *phureja* chromosome elimination in hybrid embryo—Hougas, et al., Crop. Sci. 4:593–595 (1964); Clulow, et al., Theor. Appl. Genet. 82:545–551 (1991). Regarding Canola/Rapeseed, somatic separation of the parental genomes in hybrids between *Brassica napus* and *Orychophragmus violaceous* is described in Li, Z., et al., *Theor. Appl. Genet.* 91:131–136 (1995); Li, et al., *Hereditas* 125:69–75 (1996); Li, et al., *Theor. Appl. Genet.* 96:251–265 (1998); Wu, J., et al., *Plant Breeding* 116:251–257 (1997). The hybrid is morphologically intermediate but is self-fertile and upon selfing produces mostly *B. napus* progeny. *Orychophragmus* method works also with *Brassica juncea* and *Brassica carinata,* two other *Brassica* species of economic importance. It will also operate with other economically crucifers such as *B. oleracea, B. campestris, Raphanus sativus.* Regarding soybean, wild species genome elimination in the progeny of a hybrid between soybean and *Glycine tomentella* is documented in Shoemaker, et al., *Theo. Appl. Genet.* 80:17–23 (1990). Yet other examples of matroclinous plants result from crosses between *Fragaria vesca* (strawberries) and *Fragaria chiloens* or *F. virginiana* (Ichijima, *Genetics,* 11:590–604 (1926)) as well as patroclinous plants from crosses between *Nicotiana digluta* and *N. tabacum* (tobacco, Clausen and Lammerts, *Amer. Nat.* 63:279–322 (1929)).

Insofar as monocotyledonous crops are concerned, Galinat, *Ann. Rev. Genet.,* 5:447–478 (1971) and Galinat, *Evolution,* 27:644655 (1973), demonstrated that in a cross between a diploid maize and a diploid *Tripsacum dactyloides,* the $F_1$ hybrid had the expected amphi-haploid chromosome number. *Tripsacum* chromosomes could not pair in meiosis, however, and since *Tripsacum* chromosomes tend to be lost during mitosis as well as meiosis, diploid maize was recovered as soon as $BC_1$. These results have been routinely reproduced in numerous breeding labs around the world. When wheat or barley is crossed with wild species *Hordeum bulbosum,* a high frequency of haploids is obtained as a result of fertilization and subsequent elimination of *bulbosum* genome (Kasha and Kao, *Nature* 225: 874–876 (1970); Barclay, *Nature* 256:410–411 (1975)). The method has been widely used for haploid production of numerous varieties of both crops. *Bulbosum* method has been replaced by wide crosses, wherein wheat (both *Triticum estivum* as well as *T. turgidum*), triticale or barley plants are pollinated by pollen of maize, sorghum, pearl millet or *Tripsacum.* The resultant hybrids are highly unstable and as a rule, developing plants retain only maternal genome. This haploidy method works with dozens of wheat varieties and is essentially variety-independent. Laurie and Bennet, *Theor. Appl. Genet.* 76:393–397 (1988); Ohkawa, et al., *Jap. J. Breed.* 42:891–894, (1992); Ushiyama, et al., *Jap. J. Breed.* 41:353–357 (1991); Furusho, et al., *Jap. J. Breed.* 41:175–179 (1991); Laurie, *Genome,* 32:1063–1067 (1989). The same method is also applicable for haploid production in oats. See, Rines and Dahleen, *Crop Sci.,* 30, 1073 (1990). Preferential genome segregation also occurs in progenies of interspecific rice (*Oryza*) combinations, such as *O. sativa* and *O. minuta.* See, Mariam, et al., *Theor. Appl. Genet.* 93:664–671 (1996).

In summary, the literature provides examples of numerous, well characterized hybridization combinations that when used in accordance with the present invention, allow for the creation of a temporary hybrid state during which heterologous genetic material may be exchanged. In addition, many wild species may be used as transgene donors for rapid and linkage drag-free transgene transfer into multiple species of important crops. Wild species include *Tripsacum* (e.g., for maize, wheat, barley and oats); *Oryza minuta* (e.g., for rice), *Orychophragmus* (e.g., for canola and other economically important crucifers); *Solanum phureja* (e.g., for potato), and *Glycine tomentella* (e.g., for soybean). Mutants such as a semigamy mutant of cotton or a ms mutation causing polyembryony in soybean may also be used for the same purpose. Similar species combinations or mutants may be easily identified for other important crop species including sugar beets, peas and tomatoes. The donor species is transformed with an exogeneous or heterologous construct that contains genetic information, the genetic instructions necessary to direct the excision of the transgene in question and its reintegration into another chromosome based on either homologous or non-homologous recombination mechanisms, and the DNA of interest. To facilitate selection of successful transformants, the construct also contains DNA encoding a selectable marker such as a trait to be monitored (e.g., antibiotic or herbicide resistance or a phenotypic marker, in particular beta-glucuronidase and/or green fluorescent protein). The DNA of interest may contain one or more genes encoding different proteins. Expression of the genes in progeny of the recipient plant may result in greater resistance to fungal, viral and/or bacterial diseases, pests, insecticides or environmental stress, or may result in improved flavor, storage or nutritional properties. The recipient organism may be an untransformed plant or a plant transformed to contain in its genome specific sites necessary for homologous recombination exchange with the exogenous DNA inserts in donor genome.

In preferred embodiments, the heterologous DNA is moved from the donor to the recipient via a system based on (1) transposon-mediated non-homologous transgene transfer or (2) targeted transfer utilizing homologous recombination mechanism. Transposons are mobile genetic elements that can comprise a substantial part of the genome of a plant and create tremendous phenotypic diversity. Transposable elements are mobile segments of DNA capable of excision and reinsertion into another locus on a chromosome. Plant transposons are among first mobile DNA elements described and a number of plant transposable elements that have been cloned, such as Ac/DS, Mu and En/Spm, are preferred for use in the present invention. These transposable elements are currently used as genetic tools in plant molecular biology and biotechnology. They serve as invaluable tools for plant developmental studies and for plant genome analysis and plant gene isolation through the so-called insertional mutagenesis and tagging. See, e.g., Walbot, Ann. Rev. Plant Mol. Biol. 43:49–82 (1992). Other examples of transposable elements for use in the present invention are described in Fedoroff, U.S. Pat. No. 4,732,856; Doonerk et al., PCT Application WO91/156074; etc.), Yoder and Lassner, PCT Application WO92/01370, and Ebinuma et al., PCT Application WO96/15252.

For the purposes of the present invention, transposon-based excision and reinsertion of transgenes is a system that allows for the disconnection of the transgene movement from the resident plant gene movement during crosses while providing an additional important advantage of full instructions directing transgene excision and reinsertion in just one genetic construct and via one transformation step. Thus, the system does not require genetic engineering of landing sites in recipient organisms.

In another preferred embodiment, the heterologous DNA is integrated in a specific site of the recipient genome by use of a recombinase and recombination site combination. Site-specific recombinases from bacteriophage and yeasts are being widely used as tools for manipulating DNA both in the test-tube and in living organisms. Preferred recombinases/recombination site combinations for use in the present invention are Cre-Lox, FLP-FRT, and R-RS, where Cre, FLP and R are recombinases, and Lox, FRT, and RS are the recombination sites. Other suitable systems include the intron-encoded yeast endonuclease I-SceI, may be used. See, Choulika, et al., Mol. Cell Biol. 15:1968–1973 (1995). To be functional in plants, these sites require 7–8 base pairs (bp) of core sequence between 12–13 bp inverted repeats; the asymmetric core site determines the site orientation, and thus the types of recombination product. Regardless of whether recombination sites are placed on or within a single DNA molecule in direct or opposite orientation, or placed on unlinked linear or circular DNA molecules, the corresponding recombinase can catalyze the reciprocal exchange to produce a deletion, inversion, translocation or co-integration event. See, Bollag, et al., *Ann. Rev. Genet.* 23:199–225 (1989); Kilby, et al., *Trends Genet.* 9:413–421 (1993); and Ow, *Curr. Opinion Biotech.* 7:181–186 (1996). In the present invention, recombinase-mediated site-specific translocation occurs between different, and in particular non-homologous chromosomes. This in-trans recombinase effect is essential in order to effect transfer of transgenes between two chromosomes belonging to different parents in a hybrid. See, Dale and Ow, *Gene* 91:79–85 (1990); Odell, et al., *Mol. Gen. Genet.* 223:369–378 (1990); Dale and Ow, *Proc. Natl. Acad. Sci. USA* 88:10558–10562 (1991); Russell, et al., *Mol. Gen. Genet.* 234:49–59 (1992); Lyznik, et al., *Plant J.* 8:177–186 (1995); Albert, et al., *Plant J.* 7:649–659 (1995); van Deuersen et al., *Proc. Natl. Acad. Sci. USA* 92:7376–7380 (1995).

Examples of suitable homologous recombination systems for use in the present invention are disclosed in the literature, including the Cre-Lox system (Sauer, U.S. Pat. No. 4,959,317, Odell, et al., U.S. Pat. No. 5,658,772; Odell, et al., PCT WO91/09957) and the FLP-FRT system (Hodges and Lyznik, U.S. Pat. No. 5,527,695). One particular utility of known recombination systems for transgene management in plants is directed excision of a transgene from plant genome, a procedure that allows elimination of unwanted heterologous genetic material such as antibiotic selective markers from a commercial variety (Ow and Dale, PCT WO03/01283). These systems, however, address an entirely different utility area, namely, the use of homologous recombination to eliminate unwanted portions of heterologous DNA, rather than to manage separation of flows of transgenes and resident plant genes. Another utility is described in Hooykaas and Mozo, U.S. Pat. No. 5,635,381, and Offringa, et al., U.S. Pat. No. 5,501,967, directed to the use of homologous recombination systems to achieve a site-directed targeted integration of DNA into plant genomes via *Agrobacterium*-mediated transformation. These cases also are limited to targeted transfer between bacteria and plant cells rather than between two plant organisms.

Homologous recombination-based transgene shuffling has both clear and strong advantages. By employing precise targeting via homology-addressed DNA sites, transgene "landing sites" can be created that are carefully selected and characterized in advance. As a result, higher level of predictability and reproducibility of transgene behavior, including heritability, expression level, absence of silencing, etc., is achieved. Also, later versions of the transgene cassette can be addressed to the same site, replacing old versions of transgenes with newer ones. Subsequent breeding of the material with a preselected and determined and mapped integration sites is much easier and straightforward. Those skilled in the art will appreciate that this system can be used only if all recipients have been "pre-wired" to contain integration sites. Such as introgression is possible by using other transfer mechanisms, for example, transposon-mediated transfer or classical introgression by backcrossing. In more specific cases, a recombinase gene also can be introduced into acceptor species in addition to its recombination site. In such cases, the recombinase gene will be under control of artificial transcription factor-mediated promoter where transcription factor is constitutively expressed by the gene located in donor (clipboard) plant. Recombinase can be produced only during the co-existence of two genomes in unstable hybrids. Alternatively, recombinase can be located in clipboard plant, but the transcription factor is constitutively expressed in the recipient plant.

The heterologous DNA may be introduced into the donor plant in accordance with standard techniques. Transformation techniques for dicotyledons are well known in the art and include *Agrobacterium*-based techniques and techniques which do not require *Agrobacterium*. Non-*Agrobacterium* techniques involve the uptake of exogenous genetic material directly by protoplasts or cells. These techniques include PEG or electroporation mediated uptake, particle bombardment-mediated delivery and microinjection. Examples of these techniques are described in Paszkowski et al., EMBO J 3:2727–2722 (1984), Potrykis et al., Mol. Gen. Genet. 199:169–177 (1985), Reich et al., Biotechnology 4:1001–1004 (1986), and Klein et al., Nature 327:70–73 (1987). In each case, the transformed cells are regenerated to whole plants using standard techniques.

*Agrobacterium*-mediated transformation is a preferred technique for transformation of dicotyledons because of its high efficiency of transformation and its broad utility with many different species. The many crop species which are routinely transformable by *Agrobacterium* include tobacco, tomato, sunflower, cotton, oilseed rape, potato, soybean, alfalfa and poplar (EP 0 317 511 (cotton), EP 0 249 432 (tomato), WO 87/07299 (*Brassica*), U.S. Pat. No. 4,795,855 (poplar)). *Agrobacterium* transformation typically involves the transfer of the binary vector carrying the foreign DNA of interest (e.g., pCIB200 or pCIB2001) to an appropriate *Agrobacterium* strain which may depend on the complement of vir genes carried by the host *Agrobacterium* strain either on a co-resident plasmid or chromosomally (e.g., strain CIB542 for pCIB200 (Uknes et al., Plant Cell 5:159–169 (1993)). The transfer of the recombinant binary vector, to *Agrobacterium* is accomplished by a triparental mating procedure using *E. coli* carrying the recombinant binary vector, a helper *E. coli* strain which carries a plasmid such as pRK2013 which is able to mobilize the recombinant binary vector to the target *Agrobacterium* strain. Alternatively, the recombinant binary vector is transferred to *Agrobacterium* by DNA transformation (Hüfgen & Willmitzer, Nucl. Acids. Res. 16, 9877 (1988)).

Transformation of the target plant species by recombinant *Agrobacterium* usually involves co-cultivation of the *Agrobacterium* with explants from the plant and follows protocols known in the art. Transformed tissue is regenerated on selectable medium carrying an antibiotic or herbicide resistance marker present between the binary plasmid T-DNA borders.

Preferred transformation techniques for monocots include direct gene transfer into protoplasts using PEG or electroporation techniques and particle bombardment into callus tissue. Transformation can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al., Biotechnology 4:1093–1096 (1986)).

Published Patent Applications EP 0 292 435, EP 0 392 225 and WO 93/07278 describe techniques for the preparation of callus and protoplasts of maize, transformation of protoplasts using PEG or electroporation, and the regeneration of maize plants from transformed protoplasts. Gordeon-Kamm, et al., Plant Cell 2:603–618 (1990), and Fromm, et al., Biotechnology 11:194–200 (1993), describe techniques for the transformation of elite inbred lines of maize by particle bombardment.

Transformation of rice can also be undertaken by direct gene transfer techniques utilizing protoplasts or particle bombardment. Protoplast-mediated transformation has been described for *Japonica*-type and *Indica*-types (Zhange, et al., Plant Cell Rep. 7:739–384 (1988); Shimamoto, et al., Nature 338:274–277 (1989); Datta, et al., Biotechnology 8:736–740 (1990)). Both types are also routinely transformable using particle bombardment (Christou, et al., Biotechnology 9:957–962 (1991)).

Patent Application EP 0 332 581 describes techniques for the generation, transformation and regeneration of *Pooideae* protoplasts. Furthermore wheat transformation is described in Vasil, et al., Biotechnology 10:667–674 (1992) using particle bombardment into cells of type C long-term regenerable callus, Vasil, et al., Biotechnology 11:1553–1558 (1993) and Weeks, et al., Plant Physiol. 102:1077–1084 (1993) describe particle bombardment of immature embryos and immature embryo-derived callus.

Transformation of monocot cells such as *Zea mays* is achieved by bringing the monocot cells into contact with a multiplicity of needle-like bodies on which these cells may be impaled, causing a rupture in the cell wall thereby allowing entry of transforming DNA into the cells. See U.S. Pat. No. 5,302,523. Transformation techniques applicable to both monocots and dicots are also disclosed in the following U.S. Pat. Nos.: 5,240,855 (particle gun); 5,204,253 (cold gas shock accelerated microprojectiles); 5,179,022 (biolistic apparatus); 4,743,548 and 5,114,854 (microinjection); and 5,149,655 5,120,657 (accelerated particle mediated transformation); 5,066,587 (gas driven microprojectile accelerator); 5,015,580 (particle-mediated transformation of soy bean plants); 5,013,660 (laser beam-mediated transformation); 4,849,355 and 4,663,292.

The thus-transformed plant cells or plant tissue are then grown into full plants in accordance with standard techniques. Transgenic seed can be obtained from transgenic flowering plants in accordance with standard techniques. Likewise, non-flowering plants such as potato and sugar beets can be propagated by a variety of known procedures. See, e.g., Newell et al. Plant Cell Rep. 10:30–34 (1991) (disclosing potato transformation by stem culture).

In another embodiment of the present invention, the heterologous nucleic acid is transferred from the donor to the genome of the recipient plant via fusion of somatic cells or protoplasts. An advantage of this embodiment is that some of hybridization barriers limiting sexual crossing are bypassed. This technology is more complex than sexual crossing, however, and it can be used only for crosses between species that can be regenerated from a protoplast. Thus, it is preferred to use donor and recipient plants that are unrelated. Examples of such pairings include *Arabidopsis*/cotton, *Arabidopsis*/soybean, *Arabidopsis*/rice and tobacco/soybean. On the other hand, although hybrids between distantly related species (intergeneric, intertribal and interfamilial) have been created using protoplast hybridization, the ability of two phylogenetically distant genomes to cooperate in a hybrid cell has been limited and hybrid cells are often unstable and quickly lose genetic material of one of parental species. See, Gleba & Sytnik, *Monogr. Theor. Appl. Genet.* 8:1–220 (1984), Dudits, et al., *Proc. Nat. Acad. Sci. USA* 84:8434–8438 (1987), and Babiychuck, et al., *Mol. Gen. Genet.* 84:87–91 (1992). Thus, pairings of related donor and recipient plants that are distantly related are more preferred.

The experiments described below are summaries of successful transformation and line conversion for four important crop species (canola, potato, maize and wheat) based on use of specific species hybridization combinations and either transposon- or homologous recombination-based transgene excision/reinsertion. These examples are presented merely to illustrate specific embodiments of the present invention, and are not intended to provide any limitation to the invention not set forth in the claims.

EXAMPLES

Example I

Transformation/line conversion of *Brassica* species

Designing the constructs

Binary vectors containing components of *Z. mays* transposable element Spm within T-DNA borders were made as described below.

Plasmid pIC012 was digested with XhoI and SmaI, large fragment was gel purified and ligated with RS fragment produced by XhoI and ClaI/Klenow treatment. Resulting plasmid pIC013, containing pNOS-RS-3'OCS in pUC118, was digested with PstI and BclI, gel-purified and ligated with large fragment of pIC017 digested with the same enzymes. Plasmid pIC23, containing dSpm element with pNOS-RS-3'OCS was consequently treated with HindIII/Klenow and BamH1/Klenow in order to remove HindIII and BamH1 sites. Large ClaI fragment of pIC23 (-BamH1;-HindIII) was cloned in ClaI site of pIC201, giving dSpm element flanked by p35S and GUS-3'NOS (pIC132). Plasmid pIC132 was digested with EcoR1 and HindIII. Large fragment was gel-purified and cloned into EcoR1 and HindIII sites of binary vector based on pRK290 and carrying NPTII gene as the plant transformation marker. Resulting plasmid pIC141 was digested with Ecl136II and HindIII, ligated with 0.3 kb XhoI—BamH1 fragment of pIC022 and 7.7 kb XhoI-SmaI fragment of pIC023 in order to introduce Spm transposase under control of 35S promoter into the binary vector. Plasmid pIC156 was obtained and used in transformation experiments. Plasmid pIC216 was made in similar way, but XhoI—BamH1 fragment of pIC022 was replaced by 0.2 kb XhoI-BglII fragment (pSpm) of pIC61.

Cloning steps for another four vectors were only different from the described above by the stages of equipping dSpm element with either pNOS:BAR-OCS3' or with pNOS:BAR-OCS3' where BAR was flanked by two RS sites. The plasmid pIC132 was digested with Pst1, BclI, gel-purified and ligated with 1.5 kb Pst1, BclI fragment of pIC016, giving the dSpm element with pNOS:BAR-OCS3'.

For constructs pIC401 and pIC411 large XhoI-NcoI fragment of pIC01 was ligated with small fragment of BspH1—BamH1 fragment of pIC018 and two RS fragments flanked with NcoI-BspH1 and Bgl11-XhoI sites respectively. Resulting plasmid pIC38 consists of BAR gene flanked by two RS sites. Small XhoI fragment of pIC36 was recloned into XhoI site of pIC334 giving plasmid pIC342 with pNOS:RS-BAR-RS-OCS3'. The last cassette was re-cloned into dSpm element as described above.

Figure 3:
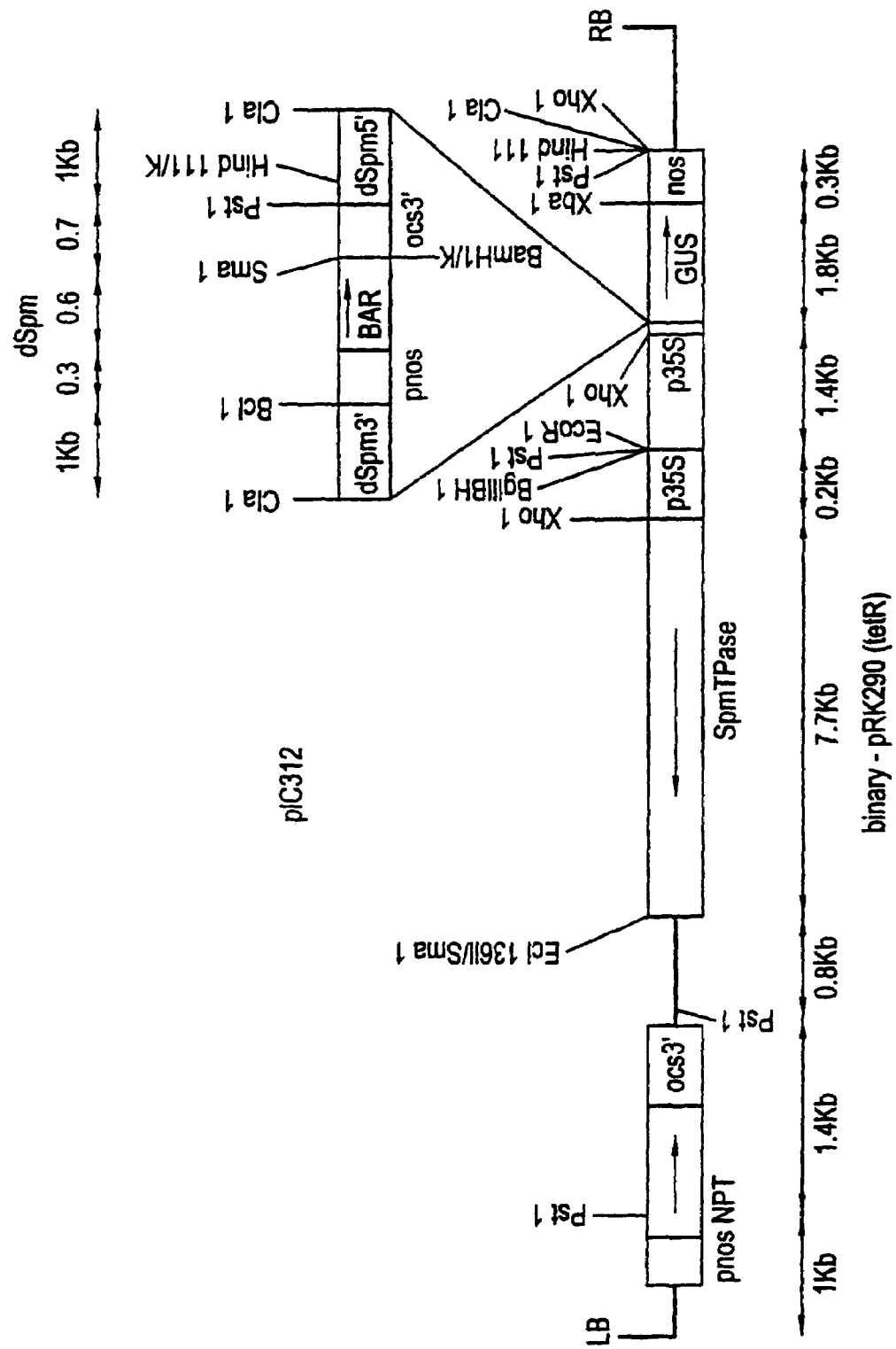
FIG. 3 is a linear plasmid map of pIC312.
Figure 4:
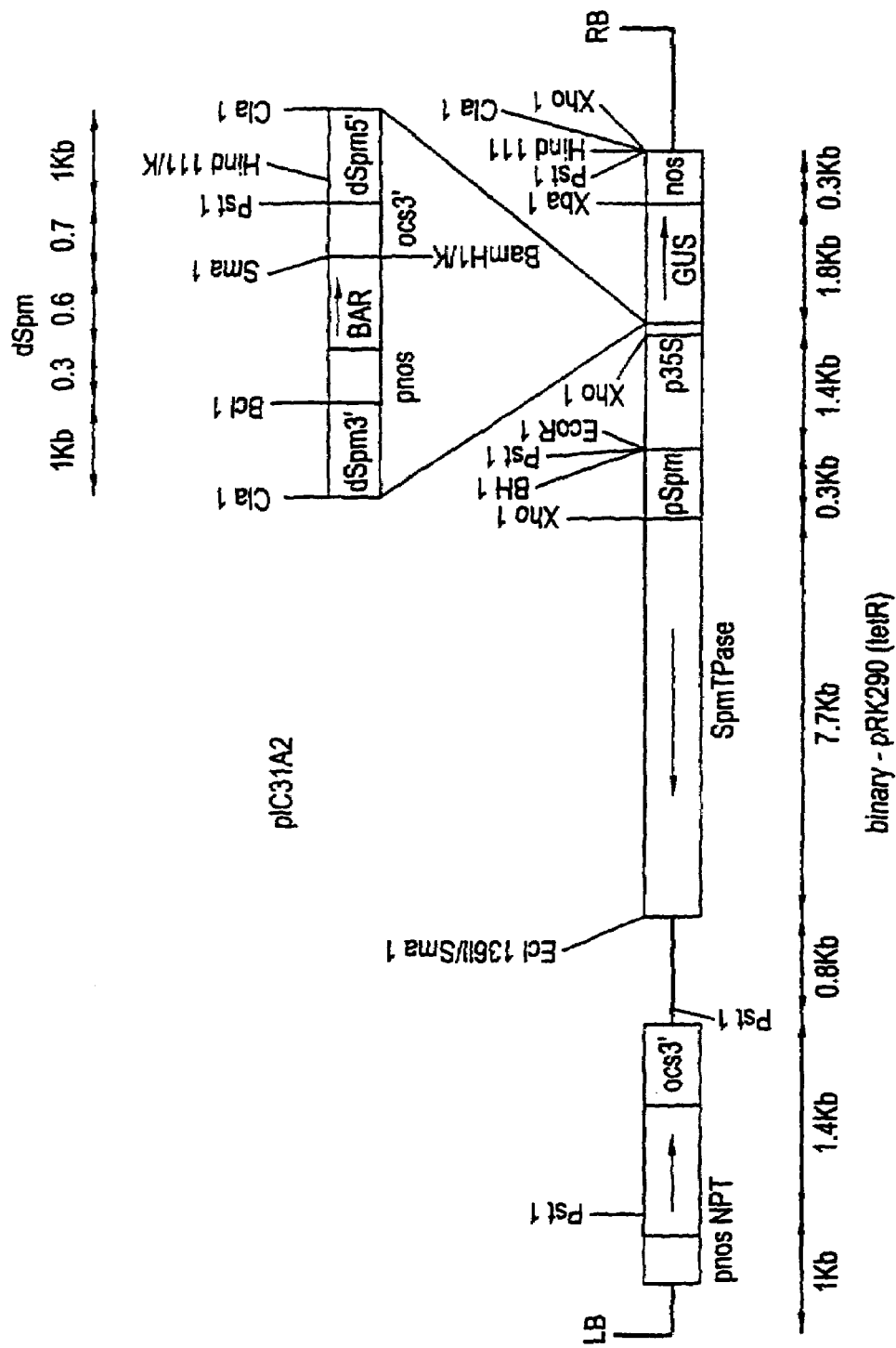
FIG. 4 is a linear plasmid map of pIC31A2.
Figure 5:
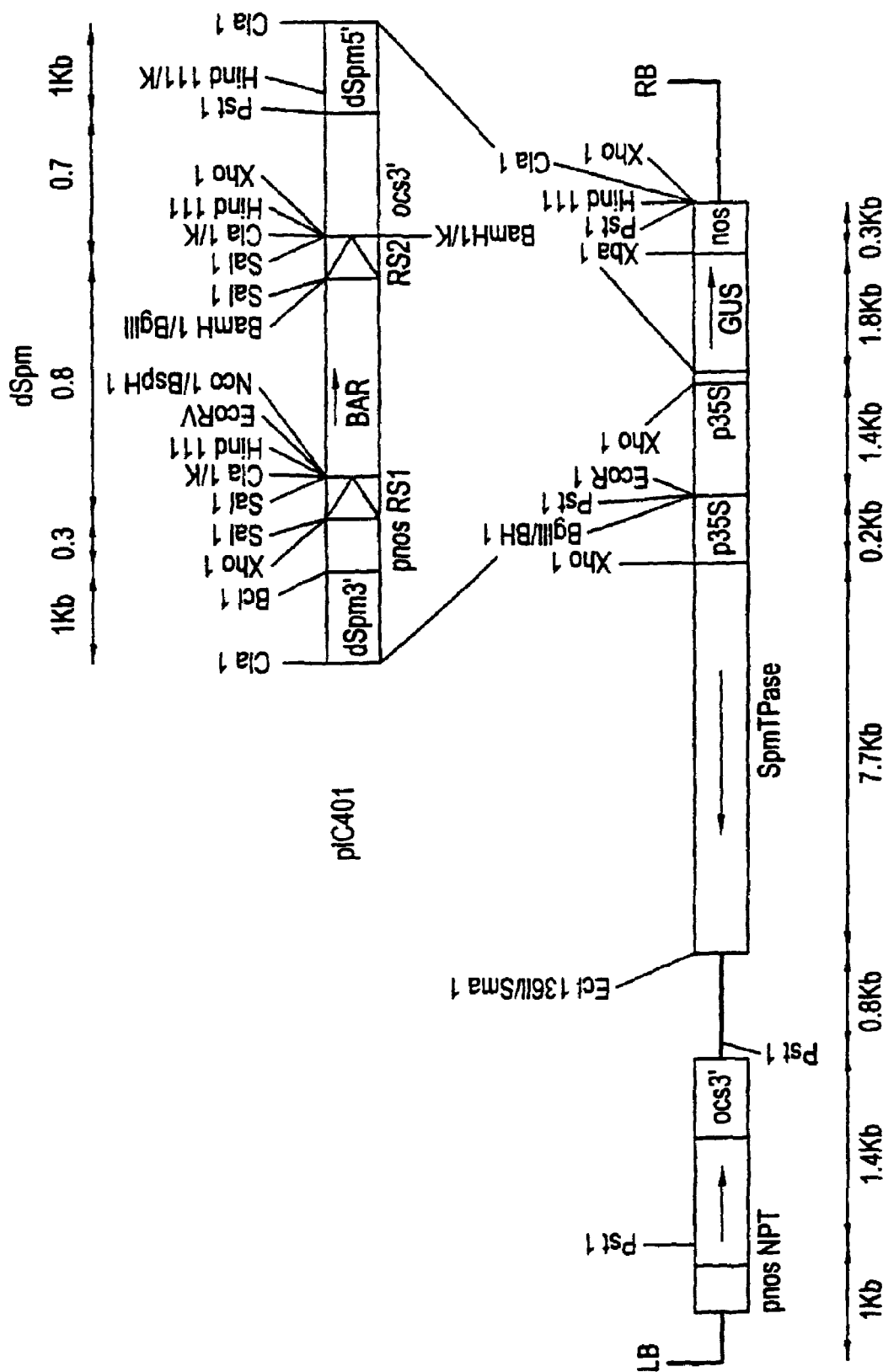
FIG. 5 is a linear plasmid map of pIC401.
Figure 6:
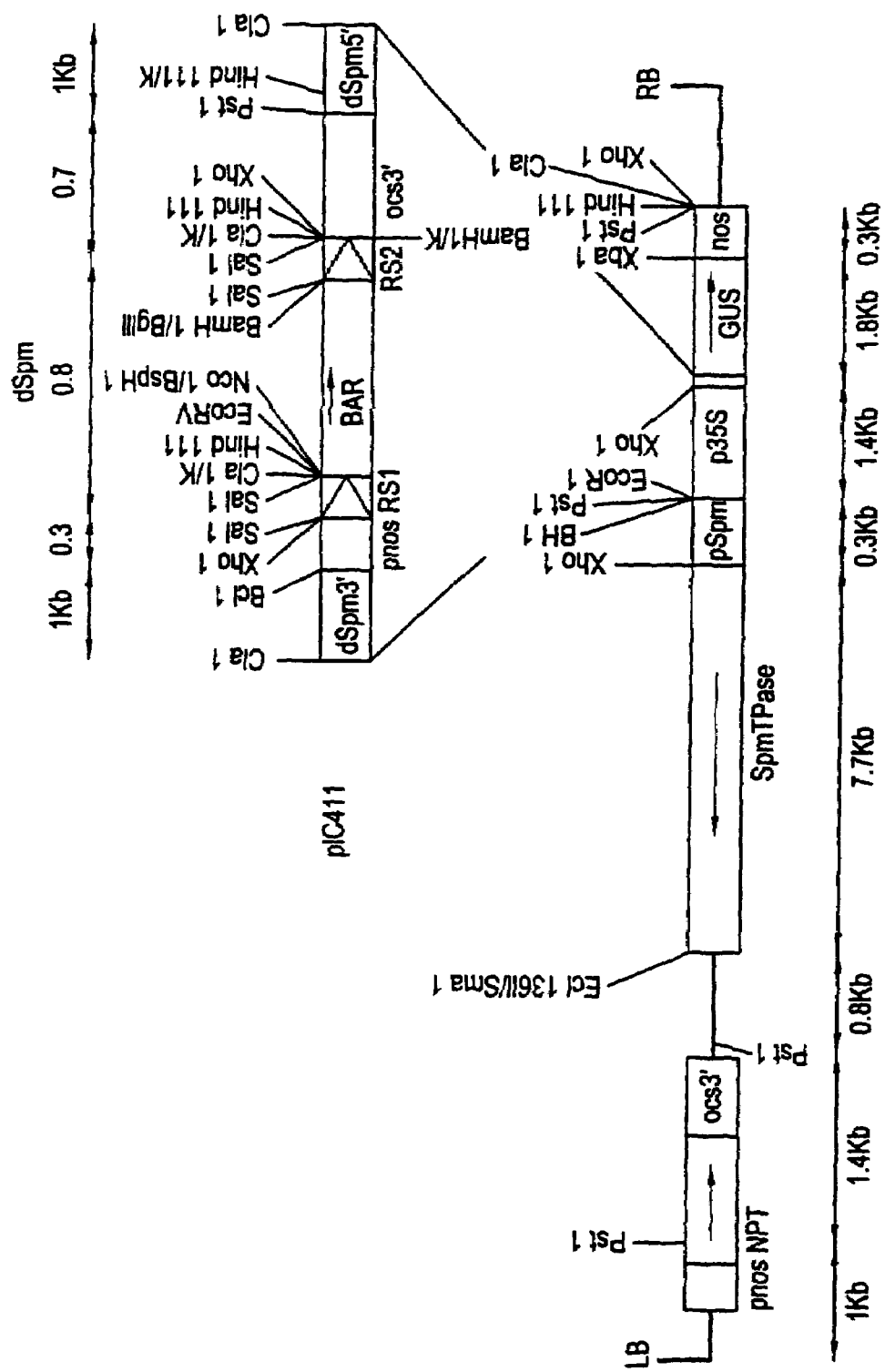
FIG. 6 is a linear plasmid map of pIC411.

In summary, constructs obtained consist of transformation marker (NPTII) gene conferring resistance to kanamycin), source of Spm transposase under control of either 35S or its own promoter, non-autonomous dSpm element inserted within p35S:GUS excision marker. Three different versions of dSpm element were made:

a) dSpm contains NOS promoter separated by RS site (recombination site recognized by R recombinase from *Z. rouxii*) from the terminator of transcription of OCS gene. (See: pIC156 and pIC216, FIGS. 1 and 2).

b) dSpm contains pNOS:BAR-OCS3', (pIC312, pIC31A2, FIGS. 3 and 4).

c) dSpm contains pNOS:BAR-OCS3', but BAR gene is flanked by two unidirected RS sites (pIC401, pIC411, FIGS. 5 and 6).

Constructs were tested in *Arabidopsis* using in planta transformation procedure. The dSpm excision can be easily monitored in primary transformants by the presence of GUS+ sectors after staining of plant tissues with X-gluc. All constructs showed high transposition activity in *Arabidopsis* and were used to obtain and characterize several *Orychophragmus violaceus* transformants.

Line conversion using *O. violaceus*.

Seed of *Orychophragmus violaceous* were sterilized and germinated in vitro. The transformation of in vitro grown plants of the species has been done as previously described for *Brassica* species (De Block, et al., *Plant Physiol.*, 91, 694–701 (1989). The constructs used were *Agrobacterium*-based carrying Spm transposase along with different versions of non-autonomous dSpm element inserted between 35S CaMV promoter and GUS gene (see FIG. 1). The plasmids were used to produce transformed *Orychophragmus* plants. Several transgenic plants have been produced and characterized. Two independent transformants containing a single copy insertion have been crossed as male parents to different *Brassica* species (*B. nigra, B. juncea, B. napus, B. carinata*) and *Sinapsis alba* as previously described. In total, approximately 600 crosses were done. The resultant hybrids were allowed to self and the $F_1$ progeny were selected for the presence of dSpm element (PCR analysis or phosphinotricin resistance). Those surviving selection were further screened for pure *Brassica* phenotype and for absence of GUS activity, and, finally, tested for absence of either transposase sequences, or species-specific *Orychophragmus* repeats. Finally, co-segregation of dSpm with a *Brassica* chromosome-specific RFLP pattern was established by analyzing the $F_2$ progeny.

Line conversion using *Arabidopsis thaliana*

In the examples that follow, all experiments were performed as described above except that instead of *O. violaceus*, *A. thaliana* plants were used as male parents. *Arabidopsis* is easy to transform and has short life cycle. These features make *Arabidopsis* excellent candidate for the clipboard species.

Example II

Transformation/line conversion of *Brassica napus*

Seed of *Brassica napus*, var. and those of *Orychophragmus violaceous* are sterilized and germinated in vitro. Transformation is performed as described in De Block, et al., *Plant Physiol.* 91:694–701 (1989). *Orychophragmus* seed is transformed with *Agrobacterium*-based vector pII2 containing gene for R recombinase and a promoterless gene for hygromycin resistance flanked by two rsx recombination sites. Rape seed organism is transformed with vector pII3 containing a 35S CaMV promoter with a RS recombinant site, so that proper recombination creates an active HPT gene conferring hygromycine resistance. Two independent transformed plants of each species are selected based on molecular analysis of the transgenics. Crosses and analysis of the progeny were performed as in Example I.

Example III

Transformation/line conversion of potato

Experiments are performed as above (Example I) except transgenic *Solanum phureja* is used as a pollen partner. The crosses are performed as described in Hermsen, et al., *Euphytica* 22:244–259 (1973), and primary converted lines are selected as $F_0$ diploidized dihaploids.

Example IV

Transformation/line conversion of maize

Figure 2:
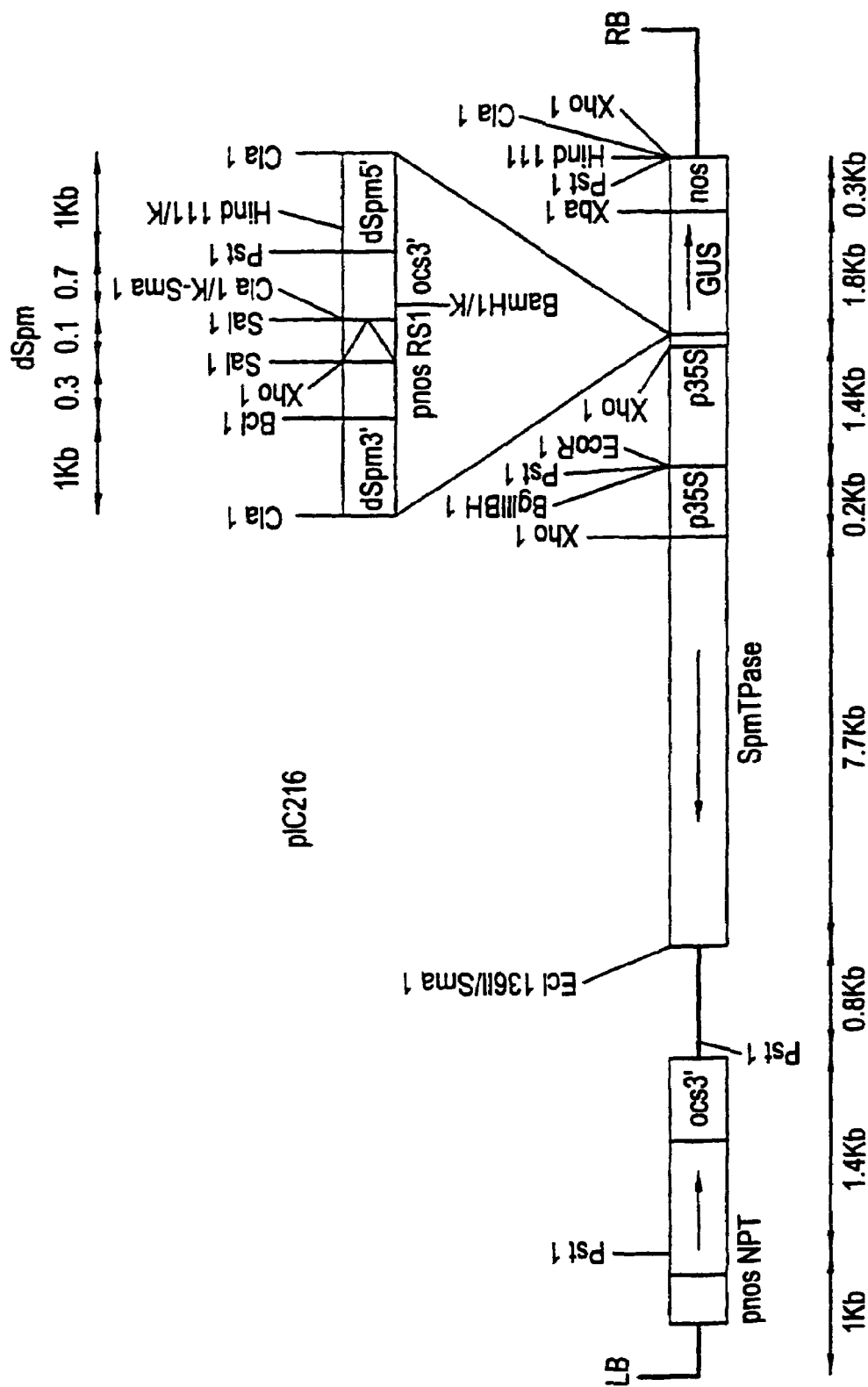
FIG. 2 is a linear plasmid map of pIC216.

*Tripsacum dactyloides* line is used in this experiment as a transgene donor. The constructs used are *Agrobacterium*-based as shown in FIG. 1, carrying Spm transposase along with non-autonomous dSpm element inserted between 35S CaMV promoter and GUS gene, the dSpm containing either one RS recombination site or one selectable marker (BAR) with (pIC401, pIC411) or without (pIC312, pIC31A2) RS sites. Transformation of the parental material is essentially performed as described in Hiei, et al., *Plant Mol. Biol.* 35:205–218 (1997). Transgenic plants are crossed with maize, var., and the resultant progeny is selfed. Pure maize-type segregates are screened from among the $BC_1$ that showed phyosphinotricin resistance or dSpm-specific PCR signal. Those surviving selection are further screened for pure maize phenotype and for absence of GUS activity, and, finally, tested for absence of either transposase sequences, or species-specific *Tripsacum* repeats. Finally, co-segregation of either phosphinotricin resistance or dSpm-specific PCR signal with a maize chromosome-specific RFLP pattern is established by analyzing the $BC/F_2$ progeny.

Example V

Transformation/line conversion of wheat

The experiments are performed as in previous example (Example IV) except the crosses are performed as described in Riera-Lizararu & Mujeeb-Kazi, *Crop Sci.* 33:973–976 (1993). Primary converted lines are selected as $F_0$ diploidized haploids emerging from the crosses.

INDUSTRIAL APPLICABILITY

The present invention is useful in the production of genetically engineered plants that exhibit a wide array of properties that may include enhanced resistance to viruses, fungi, bacterial diseases, pests, pesticides or environmental stress, as well as for the enhancement of other commercially desirable properties such as improved flavor, storage or nutritional properties.

All publications mentioned in this specification are indicative of the level of skill of persons skilled in the art to which this invention pertains. All these publications are herein incorporated by reference to the same extent as if each individual publication was specifically and individually indicated to be incorporated by reference.

Various modifications of the invention described herein will become apparent to those skilled in the art. Such modifications are intended to fall within the scope of the appending claims.

The invention claimed is:

1. A method for introducing genetic material into plants, comprising:
   preparing a first plant transformed with a heterologous nucleic acid having 5' and 3' excisable flanking sequences that comprise a transposable element, and that allow movement of said heterologous nucleic acid from one genome to another;
   crossing a second plant and the transformed first plant, wherein said first and second plants, upon crossing, produce unstable progeny or demonstrate preferential segregation or sorting out; and
   selecting progeny of said second plant of (b) which contain said heterologous nucleic acid;
   wherein said first plant, said second plant or both said first plant and said second plant produce a transposase specific to said transposable element.

2. The method of claim 1, wherein said heterologous nucleic acid further comprises a recombination site and wherein said first plant, said second plant or both said first and second plants produce a recombinase specific to said recombination sites.

3. The method of claim 1, wherein said first plant is *Tripsacum* and said second plant is maize.

4. The method of claim 1, wherein said first plant is *Tripsacum* and said second plant is wheat.

5. The method of claim 1, wherein said first plant is *Tripsacum* and said second plant is barley.

6. The method of claim 1 wherein said first plant is *Tripsacum* and said second plant is oat.

7. The method of claim 1, wherein said first plant is *Orychophragmus* and said second plant is a crucifer.

8. The method of claim 1 wherein said first plant is *Arabidopsis* and said second plant is a crucifer.

9. The method of claim 7 wherein said crucifer is canola.

10. The method of claim 1, wherein said first plant is *Glycine tomentella* and said second plant is soybean.

11. The method of claim 1, wherein said first plant is *Solanum phreja* and said second plant is potato.

12. The method of claim 1, wherein said first plant is maize and said second plant is wheat.

13. The method of claim 1, wherein said first plant is maize and said second plant is barley.

14. The method of claim 1, wherein said first plant is maize and said second plant is oats.

15. The method of claim 1, wherein said first plant is *Pennisetum* and said second plant is wheat.

16. The method of claim 1, wherein said first plant is *Pennisetum* and said second plant is barley.

17. The method of claim 1, wherein said first plant is *Hordeum bulbosum* and said second plant is barley.

18. The method of claim 1, wherein said first plant is *Hordeum bulbosum* and said second plant is wheat.

19. The method of claim 1, wherein said first plant is *Oryza minuta* and said second plant is rice.

20. The method of claim 1, wherein said first plant is *Nicotiana dilguta* and said second plant is *Nicotiana tabacum*.

21. The method of claim 1, wherein one or both said first and second plants is cotton carrying a Se semigamy mutation.

22. The method of claim 1, wherein one of said first and second plants is soybean carrying a ms mutation causing polyembryony.

23. The method of claim 1, wherein said first plant is *Arabidopsis*.

* * * * *